United States Patent [19]

Diehl et al.

[11] Patent Number: 5,068,428
[45] Date of Patent: Nov. 26, 1991

[54] PROCESS FOR THE PREPARATION OF CYCLOPROPANECARBOXAMIDE

[75] Inventors: Herbert Diehl, Leverkusen; Heinz U. Blank, Odenthal-Gloebusch; Edwin Ritzer, Gladbeck, all of Fed. Rep. of Germany

[73] Assignee: Bayer Aktiengesellschaft, Leverkusen, Fed. Rep. of Germany

[21] Appl. No.: 588,251

[22] Filed: Sep. 26, 1990

Related U.S. Application Data

[63] Continuation of Ser. No. 423,068, Oct. 18, 1989, abandoned.

[30] Foreign Application Priority Data

Oct. 28, 1988 [DE] Fed. Rep. of Germany ....... 3836782

[51] Int. Cl.$^5$ ............................................. C07C 231/00
[52] U.S. Cl. .................................................... 564/134
[58] Field of Search ......................................... 564/134

[56] References Cited

U.S. PATENT DOCUMENTS 4,590,292  5/1986  Blackwell et al. ..................... 564/1

FOREIGN PATENT DOCUMENTS 1171098  7/1984  Canada .
0205403  12/1986  European Pat. Off. .
1939759  3/1970  Fed. Rep. of Germany .
1257097  12/1971  United Kingdom .
1304667  1/1973  United Kingdom .

*Primary Examiner*—Richard L. Raymond
*Assistant Examiner*—Scott C. Rand
*Attorney, Agent, or Firm*—Sprung Horn Kramer & Woods

[57] ABSTRACT

Cyclopropanecarboxamide can be prepared by reaction of a cyclopropanecarboxylic ester with $NH_3$, in which the ester alcohol has 4–8 C atoms and can be straight-chain or branched and which process is carried out in the presence of catalytic amounts of an alkali metal alcoholate of a monohydric $C_1$-$C_8$ alcohol at 60°–200° C. in the absence of a hydrocarbon solvent.

6 Claims, No Drawings

PROCESS FOR THE PREPARATION OF CYCLOPROPANECARBOXAMIDE

This is a continuation of application Ser. No. 423,068, filed Oct. 18, 1989, now abandoned.

BACKGROUND OF THE INVENTION

1. Field of Invention

The present invention relates to a process for the preparation of cyclopropanecarboxamide by reaction of cyclopropanecarboxylic esters with $NH_3$ in the presence of catalytic amounts of an alcoholate and in the absence of a hydrocarbon solvent.

Cyclopropanecarboxamide is an organic intermediate which, for example after conversion to cyclopropylamine, is reacted to give active compounds in the pharmaceutical and plant protection sector. Such a use requires that all intermediates be prepared in high purities, which have not been achieved in previous preparative processes, so that additional, yield-reducing purification steps had to be carried out subsequently.

2. Description of the Related Art

The reaction of esters with ammonia to give the corresponding amides is generally known; in the known cases, a solvent or solvent mixture is always used.

Thus, according to DE-OS (German Published Specification) 1,939,759 (equivalent to U.S. Pat. No. 3,711,549), a mixture of 0.15 mol of sodium methoxide and 0.95 mol of methyl cyclopropanecarboxylate is reacted in 40 ml of methanol and 390 ml of toluene with ammonia at about 80° C. This gives a conversion of 85-90%; however, this result is only achieved, if the preferred methanol concentration of 40-80 ml/mol of the ester, which in turn is used in a 20-25% strength solution in toluene, is maintained. If the toluene is left out, lower yields of amide are obtained. Likewise, the degree of conversion drops to about 59%, if methanol is left out. In a variation of the procedure on a large industrial scale, the operating pressure reaches 28 atm. The conversion rate of 90%, which is the optimum obtainable under these conditions, makes a workup by distillation necessary, in which methanol, toluene and unconverted methyl cyclopropanecarboxylate have to be recycled. Water and hydrochloric acid are then added to the flask residue which is obtained in such a distillation and consists of cyclopropanecarboxamide, remaining toluene and sodium methoxide, since the amide is susceptible to hydrolysis in an alkaline, aqueous medium; the aqueous phase is separated off in a separatory funnel, and the organic phase is again extracted with water. The cyclopropanecarboxamide is then present in the highly dilute aqueous solution thus obtained.

EP 205,403 describes the reaction of sterically hindered secondary and tertiary cyclopropanecarboxylic esters with ammonia, using a different catalyst, namely the sodium salt of polyhydric alcohols, such as glycol or glycerol In this reaction, excess polyhydric alcohol has to be used to maintain a homogeneous catalyst solution. The catalyst can also be dissolved by using methanol. A further solvent used is xylene. In the workup, the polyhydric alcohol then needs to be removed azeotropically, which, in the case of glycol, is achieved, for example, by means of p-cymene, after which water is added and the p-cymene is removed azeotropically. The EP application mentioned reports operating temperatures of 100-200° C., operating pressures of up to 16 bar and yields in the range from 50-91%.

SUMMARY OF THE INVENTION

It has now been found that it is possible to go back to using conventional alcoholates of monohydric aliphatic alcohols, that is to say, to do without alcoholates of glycol or glycerol which are difficult to work up, and yet in the absence of hydrocarbon solvents, that is to say, contrary to the prior art.

One initial advantage of such a procedure is the higher space yield as a result of working with a more concentrated solution. Furthermore, the cyclopropanecarboxamide can be obtained in crystalline form and thus in very high purity. Moreover, very low operating pressures of at most 6 bar can be employed. Further advantages are evident from the description below.

The invention accordingly relates to a process for the preparation of cyclopropanecarboxamide by reaction of cyclopropanecarboxylic ester with $NH_3$ in the presence of catalytic amounts of an alcoholate, which is characterized in that a cyclopropanecarboxylic ester of the formula

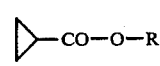 (I)

in which
R represents straight-chain or branched $C_4$-$C_8$-alkyl
is reacted in the presence of an alkali metal alcoholate of a monohydric $C_1$-$C_8$-alcohol in the absence of a hydrocarbon solvent at 60°-200° C.

DETAILED DESCRIPTION OF THE INVENTION

The ester alcohol of the cyclopropanecarboxylic ester has 4-8 atoms and is straight-chain branched. In a preferred manner, this alcohol has 4-6 C atoms, particularly preferably 4 C atoms; in a very particularly preferred manner, the isobutyl ester of cyclopropanecarboxylic acid is used.

The alkali metal of the alcoholate is lithium, sodium, potassium, rubidium or cesium, preferably sodium or potassium, particularly preferably sodium. The alcoholate alcohol has 1-8, preferably 1-6, particularly preferably 1-4, C atoms and is straight-chain or branched. In a very particularly preferred manner, sodium isobutoxide is used. A further preferred embodiment uses the same alcoholate alcohol, such as is present in the ester. The use of isobutoxide in combination with isobutyl cyclopropanecarboxylate is very particularly preferred. The alcoholate is used in an amount of 2-20 mol %, preferably 4-16 mol %, particularly preferably 6-14 mol %, relative to the number of moles of the ester to be converted.

The process according to the invention is carried out in the absence of a hydrocarbon solvent. The process according to the invention is furthermore carried out in such a manner that the amount of the alcohol present at the beginning of the reaction is such as is necessary for handling the alcoholate, for example for metering it into the reaction mixture. For example, many alcoholates, such as sodium methoxide, can be handled in solid form without any alcoholic auxiliary solvents whatsoever. In the case of higher alcoholates, it is often favourable to meter in melts consisting of a mixture with the underlying alcohol; an example of such a mixture is a 35% by weight melt of sodium isobutoxide in isobutanol. In the case where an alcoholic auxiliary solvent for the alcoholate is used, a general example is a 25-50% by weight solution or melt in an alcohol, preferably such a solution or melt in the alcohol on which the alcoholate is based. The presence of further alcohol in the course of carrying out the process according to the invention can be disregarded, since in any ammonolysis of esters the ester alcohol is cleaved off and is present in free form.

The process according to the invention is carried out at 60°-200° C., preferably at 70°-160° C., particularly preferably at 80°-140° C. By excluding hydrocarbon solvents, the solubility of ammonia in the reaction mixture is considerably higher, leading to a smaller increase in pressure. This effect is reinforced further by ammonia being continuously added, preferably at the rate at which the reaction progresses. The process according to the invention accordingly is further distinguished by being carried out at a maximum pressure of 6 bar, making it possible to work with apparatuses having lower safety requirements.

The reaction batch is worked up by first cooling it, in the course of which crystalline cyclopropanecarboxamide already precipitates The crystallization is completed in the vicinity of room temperature, that is to say, at 5°-30° C., and the crystals are separated from the mother liquor in a known manner, for example by filtration, centrifugation or decanting. The crystals can be washed by means of cold alcohol, preferably the ester alcohol. The amount of this alcoholate is such that, taking into account the ester alcohol cleaved off, the saturation concentration of the alcoholate in the cooled reaction mixture is not exceeded. The yield obtainable in such a procedure is about 90% at more than 99% conversion. In addition to the analytically pure crystallized cyclopropanecarboxamide, a mother liquor is obtained which contains remaining cyclopropanecarboxamide, ester alcohol which has been cleaved off and the alcoholate. This mother liquor can be concentrated and, after adding cyclopropanecarboxylic ester, recycled into the ammonolysis reaction. In this case, the yield is almost quantitative. When the mother liquor is concentrated for the purpose of recycling, apart from the excess ester alcohol to be removed from the previous run of the process according to the invention, the total amount of water which may have entered this alcoholate-containing mother liquor is also removed as an azeotrope. In this manner, contamination, due to hydrolysis of the ester or hydrolysis of the amide for example, can be suppressed almost completely. This variation of the workup procedure is therefore preferred.

As a result of the almost complete conversion, in addition to the preferred variation of the workup procedure, it is also possible to omit the recycling of the alcoholate and to hydrolyse and neutralize the alcoholate by the addition of water and an acidic substance (for example mineral acids or acidic ammonium salts) and then to distill off the eliminated ester alcohol as an azeotrope. This procedure makes it possible to obtain an aqueous solution of the cyclopropanecarboxamide, which can, for example, be passed on directly to the Hofmann degradation to give cyclopropylamine.

The exclusion of hydrocarbon solvents does not only have the abovementioned advantages but also that of avoiding additional azeotropes during the workup and furthermore of avoiding extractions of the product which involve wash liquids, which have to be worked up, and recyclings.

EXAMPLE 1

563.1 g of isobutyl cyclopropanecarboxylate were placed in a 1.6 l autoclave. 73.3 g of 35% strength sodium isobutoxide/isobutanol melt was then added. The mixture obtained in this manner was heated to 100° C. after two pressure tests using $N_2$. This gave a slightly brownish solution. After the reaction temperature had been reached, 30 ml of $NH_3$ (=18.5 g) were injected in the form of $NH_3$ gas, which resulted in a pressure of 6 bar, which dropped fairly rapidly, so that in the period which followed a total of 180 ml $NH_3$ (=111 g) were additionally injected as a gas, until the pressure no longer dropped even after 2 hours The reaction mixture was then carefully let down while still hot and cooled. At about 70° C., the first crystals precipitated; the crystalline slurry obtained after cooling to 20° C. was filtered off with suction, the crystals were washed with 55 g of isoBuOH and dried (50° C., 300 mbar).

Yield: 296 g of cyclopropanecarboxamide (purity >99% by GC)=88% of the theoretical yield and 331 g of mother liquor.

200 g of isobutanol were distilled off from the mother liquor, and the remainder was used again in the next run; repeated addition of sodium isobutoxide was therefore not necessary.

Yield of the 2nd batch: 332 g=98% of the theoretical yield.

EXAMPLE 2

284.4 g of isobutyl cyclopropanecarboxylate were placed in a 1.0 l autoclave. 54.8 g of 35% strength sodium isobutoxide/isobutanol melt were then added. The mixture obtained in this manner was heated to 100° C. after two pressure tests using $N_2$. This gave a slightly brownish solution. After the reaction temperature had been reached, 30 ml of $NH_3$ ($\approx$18.5 g) were injected as a gas, resulting in a pressure of 6 bar, which dropped fairly rapidly, so that in the period which followed a total of 38 ml $NH_3$ ($\approx$23.5 g) were additionally injected as a gas, until the pressure no longer dropped even after 2 hours (total reaction time: 5 to 9 hours). The reaction mixture was then carefully let down while still hot and cooled. At about 70° C., the first crystals precipitated 36 g of a 40% strength aqueous $(NH_4)_2SO_4$ solution were then added to this warm reaction mixture which was still saturated with $NH_3$, and $NH_3$, isoBuOH and $H_2O$ were distilled off through a 20 cm Vigreux column, during which water was constantly added to ensure that, after most of the ammonia had been distilled off, the isoBuOH/$H_2O$ azeotrope also distilled over and a phase boundary was formed in the water separator.

After the azeotropic isoBuOH removal had been completed, removal of water by distillation was continued until a flask temperature of 140° C. had been reached (total amount of water added: 120 g; total amount of distillate: 265 g of water, isoBuOH and $NH_3$).

The reaction was then allowed to cool, the solid, crystalline contents of the reaction vessel were transferred to a glass sintered crucible and filtered off with suction.

Yield: 182.9 g of 91.2% pure moist, salt-containing, crystalline product=98% of the theoretical yield.

EXAMPLE 3

The procedure of Example 2 was repeated, except that 18 g of 50% strength sulphuric acid were added instead of the ammonium sulphate solution. The workup was carried out as in Example 2. Yield: 173.8 g of 94.2% pure moist, salt-containing, crystalline product=96.2% of the theoretical yield.

EXAMPLE 4

The procedure of Example 2 was repeated, except that 47 g of 25% strength ammonium chloride solution were added instead of ammonium sulphate and the reaction mixture thus obtained was worked up analogously. Yield: 192.0 g of 85.9% pure moist, salt-containing, crystalline product=96.9% of the theoretical yield.

EXAMPLE 5

The procedure of Example 2 was repeated, except that the amount of isobutanol/isobutoxide was replaced by 11 g of sodium methoxide. The workup was carried out as in Example 2. Yield: 177.5 g of 93.0% pure moist, salt-containing, crystalline product=97% of the theoretical yield.

COMPARATIVE EXAMPLE 1

28.7 g of 35% strength sodium isobutoxide/isobutanol melt and 285 ml of isobutanol were added to 96.4 g of isobutyl cyclopropanecarboxylate. 18.6 g of ammonia were added, and the mixture was heated to 80° C. A pressure of 4 bar was obtained. After 12 hours, the mixture was worked up to give 55.4 g of cyclopropanecarboxamide (96% of the theoretical yield). A 1.0 l autoclave was required for carrying out the reaction. The reaction product did not crystallize but could only be recovered after a complicated distillation procedure.

COMPARATIVE EXAMPLE 2

The procedure of Comparative Example 1 was repeated, except that 285 ml of xylene were added instead of isobutanol. Due to the lower solubility of $NH_3$, a pressure of 12 bar was obtained. The workup was carried out by adding an aqueous $(NH_4)_2SO_4$ solution and such an amount of water that 2 clear liquid phases were formed. The aqueous phase was concentrated until cyclopropanecarboxamide precipitated and could be filtered off. Yield: 56.3 g of cyclopropanecarboxamide (97% of theory).

We claim:

1. A process for the preparation of cyclopropanecarboxamide comprising reacting a cyclopropanecarboxylic acid ester of the formula

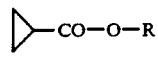

in which

R is $C_4$-alkyl, with ammonia in the presence of an alkali metal alcoholate of a monohydric $C_4$-alcohol in the absence of a hydrocarbon solvent at 60°-200° C., wherein (a) 2-20 mol % of alcoholate, relative to the number of moles of the ester to be reacted, are used, (b) the alcoholate is in the form of a 25-50% by weight alcoholic solution, and (c) alcohol is either not added at the beginning of the reaction or the amount of alcohol present at the beginning of the reaction is only such as is necessary for the handling of the alcoholate.

2. The process of claim 1, wherein the reaction is carried out at a maximum pressure of 6 bar.

3. The process of claim 1, wherein the ester alcohol radical R is isobutyl.

4. The process of claim 1, wherein the alcoholate used is sodium isobutoxide.

5. The process of claim 1, wherein after the reaction the cyclopropanecarboxamide is separated off from the reaction mixture in the form of crystals, during which the saturation concentration of the alcoholate in the reaction mixture is not exceeded.

6. The process of claim 5, wherein the reaction mixture which has been separated off from the crystals is recycled in the form of alcoholate.

* * * * *